(12) United States Patent
Metz

(10) Patent No.: US 8,875,713 B2
(45) Date of Patent: Nov. 4, 2014

(54) ANTI-OBSTRUCTIVE AIRWAY DENTAL ORTHOTIC

(76) Inventor: James Metz, Columbus, OH (US)

(*) Notice: Subject to any disclaimer, the term of this patent is extended or adjusted under 35 U.S.C. 154(b) by 190 days.

(21) Appl. No.: 13/239,498

(22) Filed: Sep. 22, 2011

(65) Prior Publication Data
US 2013/0074848 A1    Mar. 28, 2013

(51) Int. Cl.
*A61F 5/56* (2006.01)

(52) U.S. Cl.
CPC .................................. *A61F 5/566* (2013.01)
USPC .............................. 128/848; 433/68; 128/861

(58) Field of Classification Search
CPC ............ A61F 5/56; A61C 5/14; A61C 19/04; A61C 19/045
USPC .................. 128/848, 859, 861–862; 602/902; 433/5–7, 18–19, 24, 68, 140
See application file for complete search history.

(56) References Cited

U.S. PATENT DOCUMENTS

| 3,618,214 | A | * | 11/1971 | Armstrong | 433/19 |
| 3,772,789 | A | * | 11/1973 | De Weoskin | 433/5 |
| 3,916,526 | A | * | 11/1975 | Schudy | 433/8 |
| 4,505,672 | A | * | 3/1985 | Kurz | 433/6 |
| 4,708,646 | A | * | 11/1987 | Jasper | 433/19 |
| 6,012,920 | A | | 1/2000 | Woo | |
| 6,109,265 | A | * | 8/2000 | Frantz et al. | 128/848 |
| 6,295,988 | B1 | * | 10/2001 | Sue | 128/859 |
| 7,178,529 | B2 | | 2/2007 | Kownacki | |
| 7,448,388 | B2 | | 11/2008 | Halstrom | |
| 7,637,262 | B2 | | 12/2009 | Bailey | |
| 7,987,854 | B2 | | 8/2011 | Arni | |
| 2007/0224567 | A1 | | 9/2007 | Robson | |
| 2009/0007817 | A1 | | 1/2009 | Branjnovic | |

OTHER PUBLICATIONS

International Search Report and Written Opinion of the International Searching Authority for International Application No. PCT/US2012/055705, mailed Nov. 23, 2012. 8 pages.

* cited by examiner

*Primary Examiner* — Patricia Bianco
*Assistant Examiner* — Camtu Nguyen
(74) *Attorney, Agent, or Firm* — Michael J. Gallagher; David J. Dawsey; Gallagher & Dawsey Co., LPA

(57) ABSTRACT

An anti-obstructive airway dental orthotic is described. The orthotic includes a maxillary retainer and a mandibular retainer releasably attaching to a plurality of teeth of a wearer. The retainers are attached by at least one strut, either variable in length or of a plurality of lengths, which exert a forward force on the lower jaw, tending to advance the mandible relative to the maxilla. This advancement of the lower jaw promotes a less obstructed airway in the wearer, while fenestrations in the retainers may allow for greater comfort and tongue movement.

5 Claims, 9 Drawing Sheets

PRIOR ART  Fig. 1

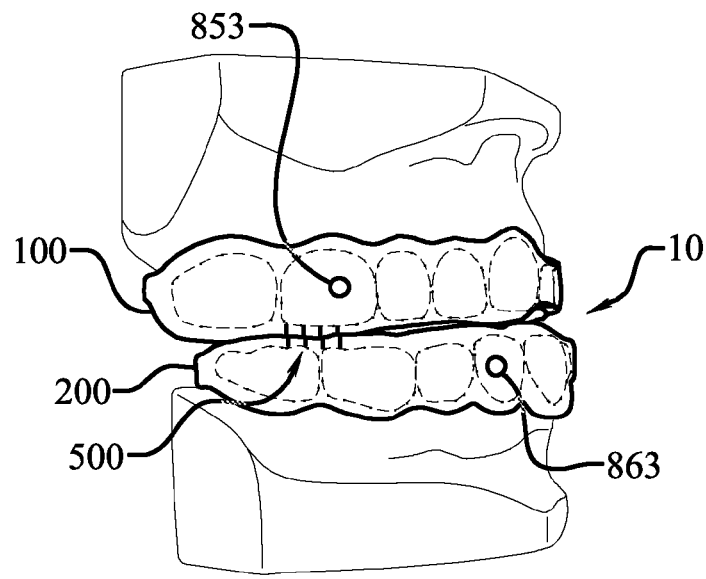
*Fig. 8*
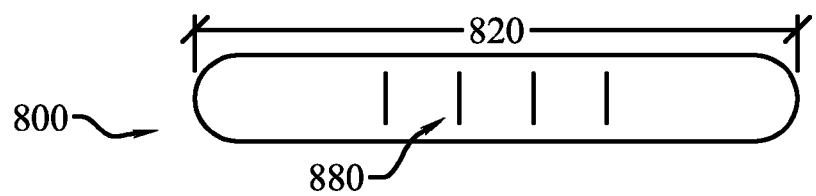
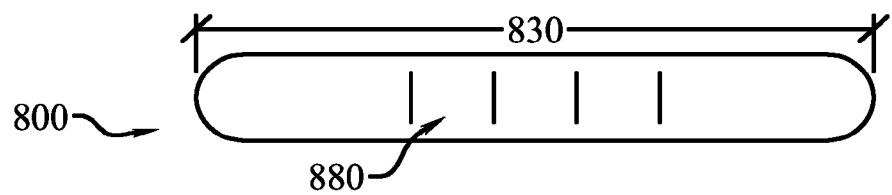
*Fig. 9*

ANTI-OBSTRUCTIVE AIRWAY DENTAL ORTHOTIC

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present disclosure relates generally to the field of dental orthotics, in particular, a means for the advancement of the lower jaw, relative to the upper.

BACKGROUND OF THE INVENTION

A large number of persons have varying degrees of upper airway obstruction presenting with varied degrees of symptoms. As the upper airway begins with the nose and mouth, it is not surprising that the nose, tongue, and jaw all make contributions to such obstructive syndromes.

Various treatment modalities have been suggested. Various airway pressure devices, such as continuous positive airway pressure devices (CPAP) have been successfully used, although these tend to be both cumbersome and uncomfortable. More recently, dental orthotics have been employed. One general class of orthotic relies upon shifting the position of the lower jaw, generally moving the jaw forward, to displace the tongue anteriorly and thereby help clear the upper airway. Obviously, it is difficult to shift the jaw anteriorly without an external anchor point, so these orthotic have also presented problems of utility and comfort.

A classical means for advancement of the jaw is the Herbst appliance, shown in general form in FIGS. 1 and 2. The Herbst appliance is a fixed, tooth-borne, functional orthodontic appliance in which jaw position is influenced by a pin-and-tube spring-loaded appliance that is cemented or bonded to the teeth.

In particular, the Herbst appliance, or Herbst-type orthotics, often suffer from a number of practical problems. Generally, these devices are semi-permanently bonded to the teeth, and while they can be removed by a practitioner, they are not generally amenable to removal by the wearer. These appliances generally cannot be adjusted as to strut length, and thus degree of jaw advancement, without removing the appliance from the mouth of a wearer.

Another class of orthotic, and in particular that described by Robson (U.S. Pat. No. 5,752,822) relies on positioning the tongue on an extension that elevates the tongue and causes the tongue to move forward to an upward position resting on the extension. These devices are designed to manipulate the airway by changing the position of the tongue.

SUMMARY OF THE INVENTION

In its most general configuration, the presently disclosed dental orthotic advances the state of the art with a variety of new capabilities and overcomes many of the shortcomings of prior devices and methods in new and novel ways. In its most general sense, the presently disclosed dental orthotic overcomes the shortcomings and limitations of the prior art in any of a number of generally effective configurations.

The dental orthotics described herein generally, in at least one embodiment, have at least a maxillary retainer for cooperating with and reversibly attaching to a plurality of maxillary teeth, a mandibular retainer for cooperating with and reversibly attaching to a plurality of mandibular teeth, and a variable-length rigid strut connecting the retainers.

The strut may have an internal strut length adjuster at least partially enclosed within the strut body and the internal strut length adjuster is adjustable to change the adjustable length when the orthotic is in a wearing position. This alone is a significant advantage over the prior art, most if not all of which require removal from a patient's mouth before strut length can be adjusted.

In an embodiment, the maxillary retainer and the mandibular retainer may be releasably and elastically joined by an elastic closure that facilitates a passive closure of the jaw. In various embodiments, the device may have jaw displacement indicia on the maxillary retainer and the mandibular retainer. As a relative anterior-posterior relationship between the maxillary retainer and the mandibular retainer changes, the position of the indicia relative to each proportionally changes, allowing a practitioner to make fine and measured adjustments in jaw displacement. The visual indicia allows relative jaw displacement to be easily seen, and thus recorded, helping provide metric guide points in the treatment of various disorders through jaw advancement.

In some embodiments, the device may have at least one maxillary fenestration, and the mandibular retainer may have at least one mandibular fenestration. These fenestrations, in at least one effect, provide for greater wearer comfort by allowing more space for tongue movement.

In another embodiment, the dental orthotic comprises at least one resilient strut attached to a maxillary retainer and a mandibular retainer. The resilient strut uses the resilience of its component material to effect a slight advancement of the jaw by placing the strut a distance slightly less than the strut length between the maxillary and mandibular retainers This shortened distance, relative to the strut length, causes a lateral deviation in the strut, which by its resilient intrinsic nature therefore applies a forward force in attempting to straighten itself.

As described previously, embodiments may include an elastic closure to promote jaw closure, and may also have at least one maxillary fenestration and/or at least one mandibular fenestration.

In such resilient strut embodiments, at least one embodiment may include jaw displacement indicia including visually perceptible resilient strut length indicia. However, these do not serve to make small mechanical adjustments to strut length, as seen with the adjustable length strut, but rather to quickly and visually indicate a relative anterior-posterior relationship between the maxillary retainer and the mandibular retainer. In the case of the resilient strut embodiments, this is to immediately and accurately identify a predetermined combination of strut length and relative jaw displacement.

Embodiments may comprise a method and system for jaw advancement utilizing a plurality of resilient struts of progressively longer length. The steps of the method may include: Molding a plurality of maxillary retainers and mandibular retainers, affixing a strut of a first length to the retainers to provide slight jaw advancement, and then observing it in use in a patient, as described above. As the jaw is advanced over time, progressively longer struts may be employed on the retainers to continue the advancement. While it would be possible to practice the method with only replacing the struts and keeping the same retainers in use, it has been found practical to mold a plurality of retainers, and then to employ new retainers with each change of strut length.

The assessment of a final desired jaw advancement may be made by a number of methods, which may include but are not limited to; subjective sense of airway improvement by the wearer, a measurement of a resting heart rate at an ambient atmosphere of the wearer, the achievement of an advancement to a predetermined amount of advancement by objective metrics, measuring and comparing resting arterial blood oxygen saturation level at an ambient atmosphere of the wearer to predetermined levels, and/or measuring and comparing a resting heart rate at an ambient atmosphere of the wearer to predetermined levels.

Numerous variations, modifications, alternatives, and alterations of the various preferred embodiments, processes, and methods may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the dental orthotic as disclosed herein and referring now to the drawings and figures:

FIG. 8 is a side view of a maxillary and a mandibular retainer of the orthotic of FIG. 7;

FIG. 9 is a side views of two embodiments of a resilient strut from the orthotic of FIG. 7;

Figure 1:
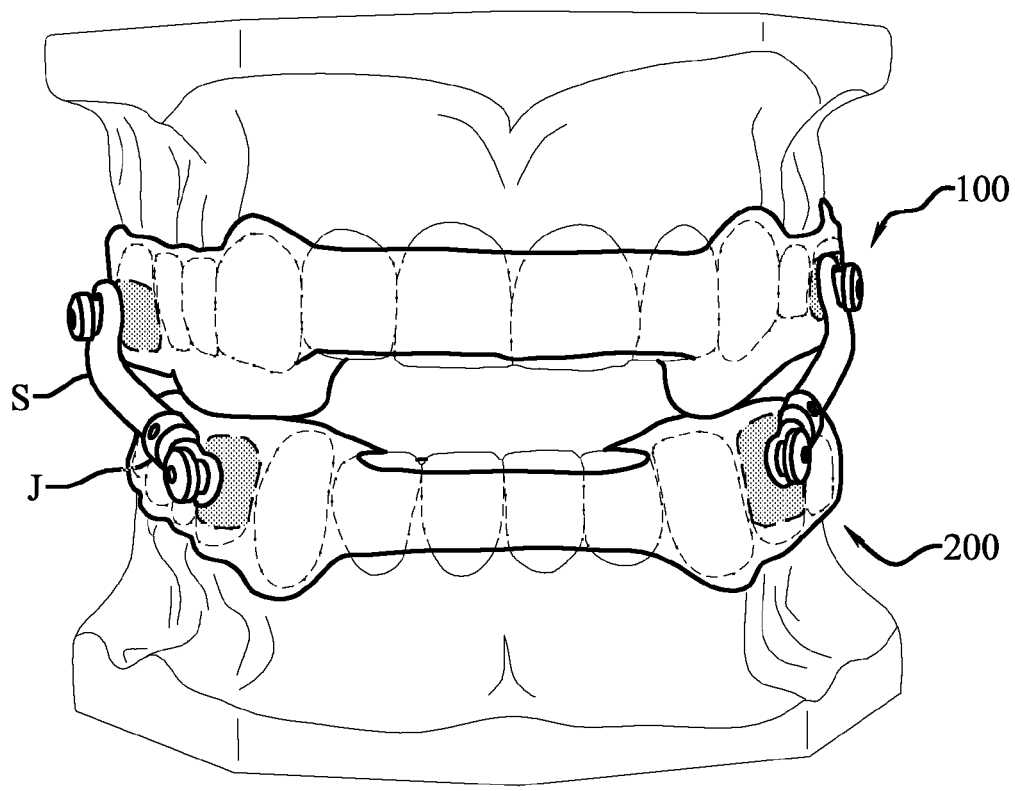
FIG. 1 is a frontal view of a prior art dental orthotic.
Figure 2:
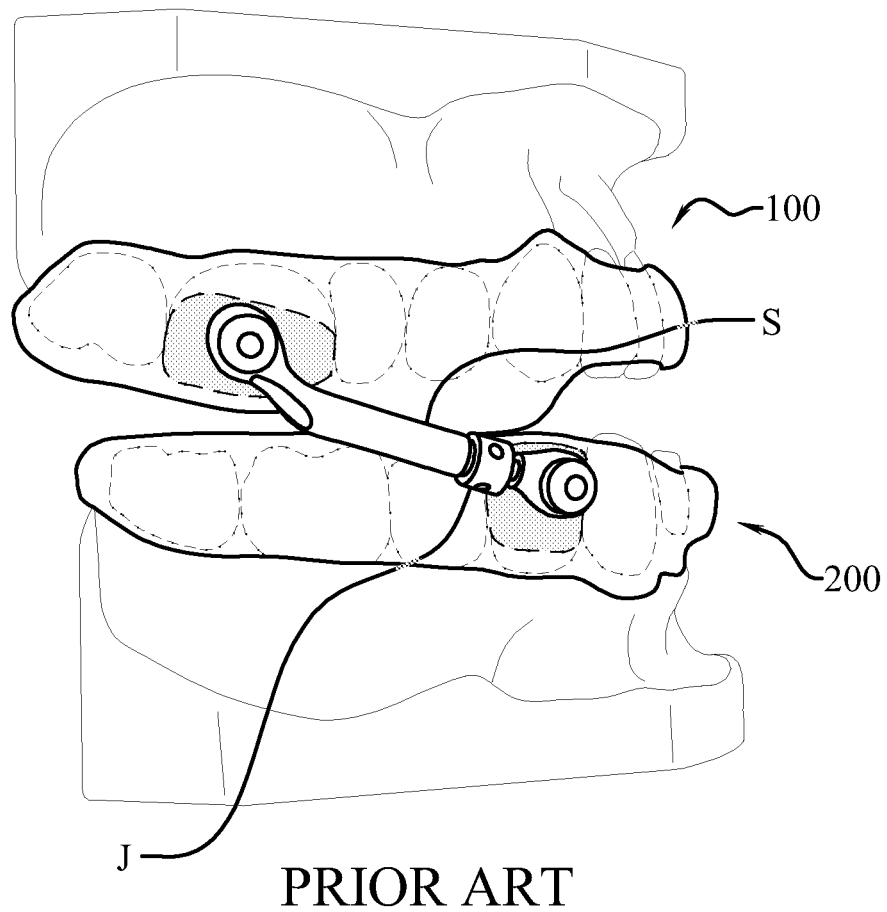
FIG. 2 is a side view of the orthotic of FIG. 1.

These drawings are provided to assist in the understanding of the exemplary embodiments of the dental orthotic as described in more detail below and should not be construed as unduly limiting the dental orthotic. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The presently disclosed anti-obstructive airway dental orthotic (10) enables a significant advance in the state of the art. The preferred embodiments of the dental orthotic (10) accomplish this by new and novel arrangements of elements and methods that are configured in unique and novel ways and which demonstrate previously unavailable but preferred and desirable capabilities. The description set forth below in connection with the drawings is intended merely as a description of the presently preferred embodiments of the dental orthotic (10), and is not intended to represent the only form in which the dental orthotic (10) may be constructed or utilized. The description sets forth the designs, functions, means, and methods of implementing the dental orthotic (10) in connection with the illustrated embodiments. It is to be understood, however, that the same or equivalent functions and features may be accomplished by different embodiments that are also intended to be encompassed within the spirit and scope of the claimed dental orthotic (10).

With reference generally to FIGS. 3-12, an anti-obstructive airway dental orthotic (10) is reversibly attached to the teeth, obviating many of the problems associated with fixed appliances. As described throughout this specification the terms anterior and posterior shall describe relative positions to each other, and shall mean as follows: Anterior shall mean more distant from a coronal, or frontal plane, relative to the term posterior, which shall mean closer to a coronal, or frontal plane. Additionally, the term practitioner shall mean any person practicing the invention, which may be, by way of example and not limitation, any one of a wide variety of health care practitioners.

Figure 3:
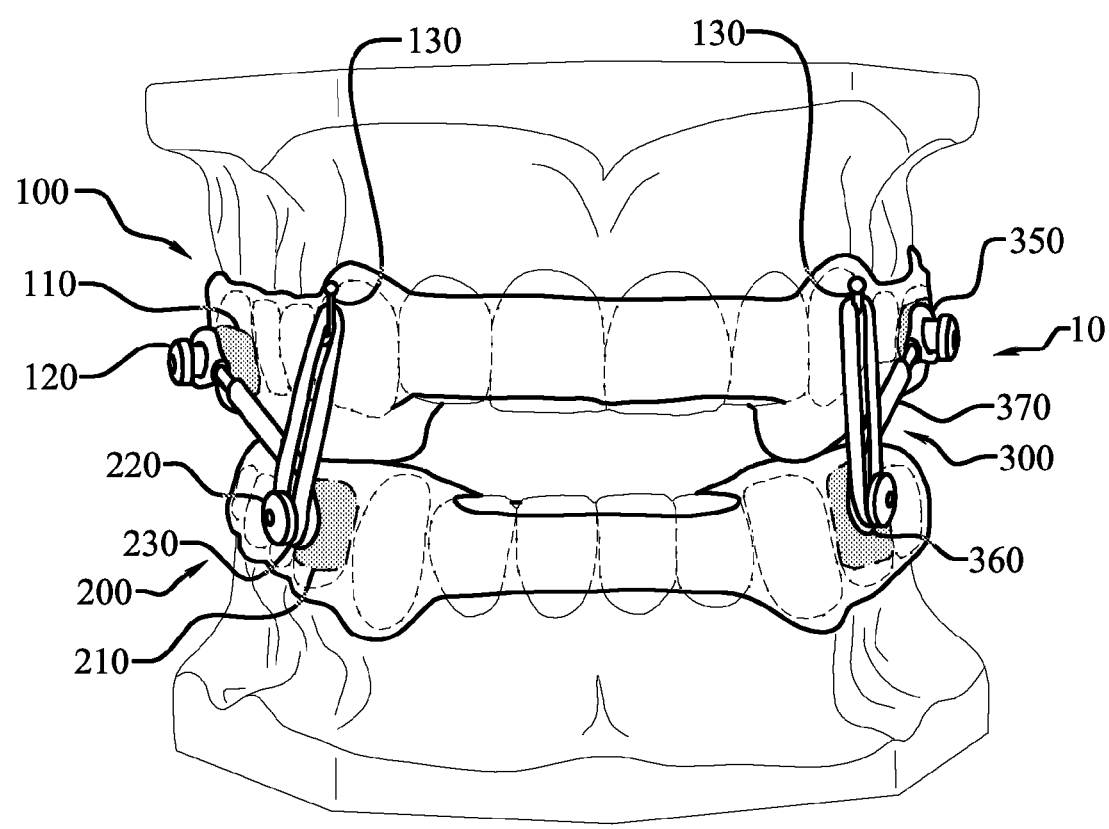
FIG. 3 is a frontal view of a dental orthotic in a wearing position.
Figure 4:
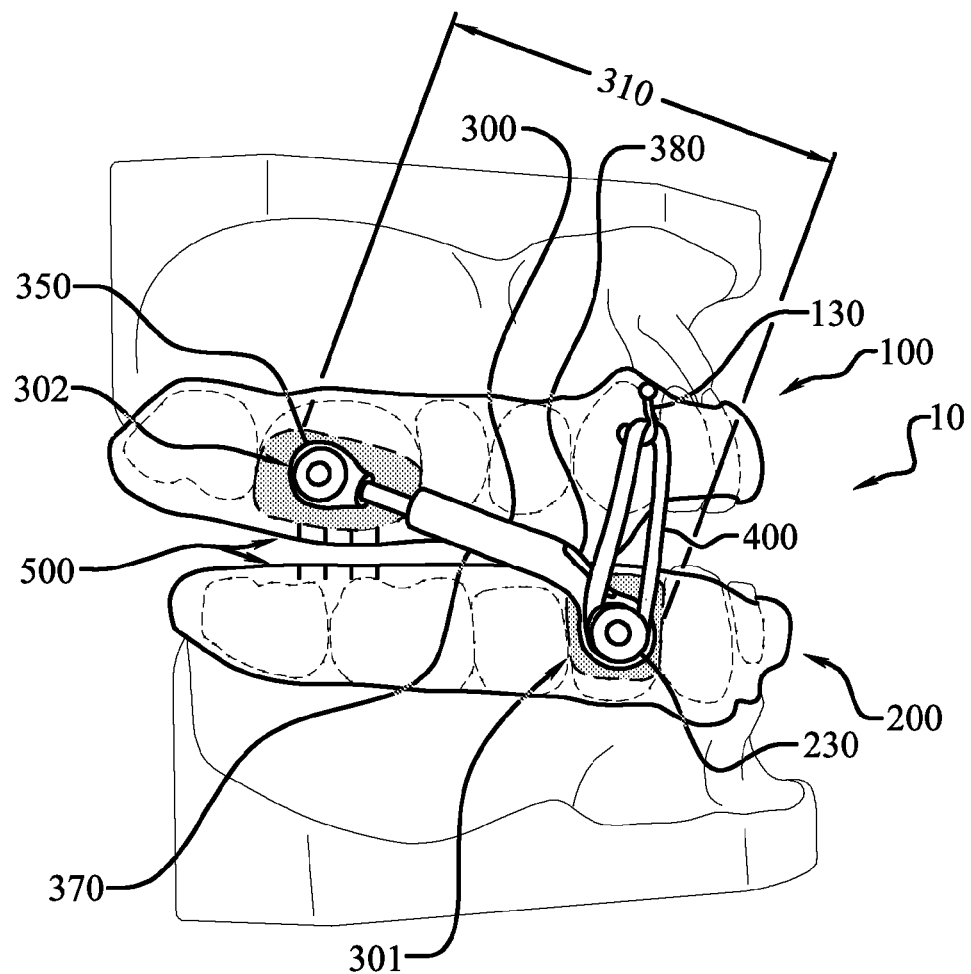
FIG. 4 is a side view of the orthotic of FIG. 3.

In one component, seen in FIGS. 3 and 4, there may be a maxillary retainer (100) for cooperating with and reversibly attaching to a plurality of maxillary teeth, and the maxillary retainer (100) includes a maxilla to strut attachment (120). In another component, there may be a mandibular retainer (200) for cooperating with and reversibly attaching to a plurality of mandibular teeth, and the mandibular retainer (120) includes a mandible to strut attachment (220).

Connecting the maxillary retainer (100) and mandibular retainer (200), there may be a variable-length rigid strut (300) including a strut body (370) having an adjustable length (310). The strut (300) may have an anterior end (301) having a strut to mandible attachment (360), and a posterior end (302) having a strut to maxilla attachment (350). The strut body (370) has an internal strut length adjuster (380) at least partially enclosed within the strut body (370) and the internal strut length adjuster (380) is adjustable to change the adjustable length (310) when the orthotic (10) is in a wearing position.

The maxilla to strut attachment (120) cooperates with the strut to maxilla attachment (350) to rotably and reversibly connect the maxillary retainer (100) and the strut (300), and the mandible to strut attachment (220) cooperates with the strut to mandible attachment (360) to rotably and reversibly connect the mandible retainer (200) and the strut (300).

Figure 5:
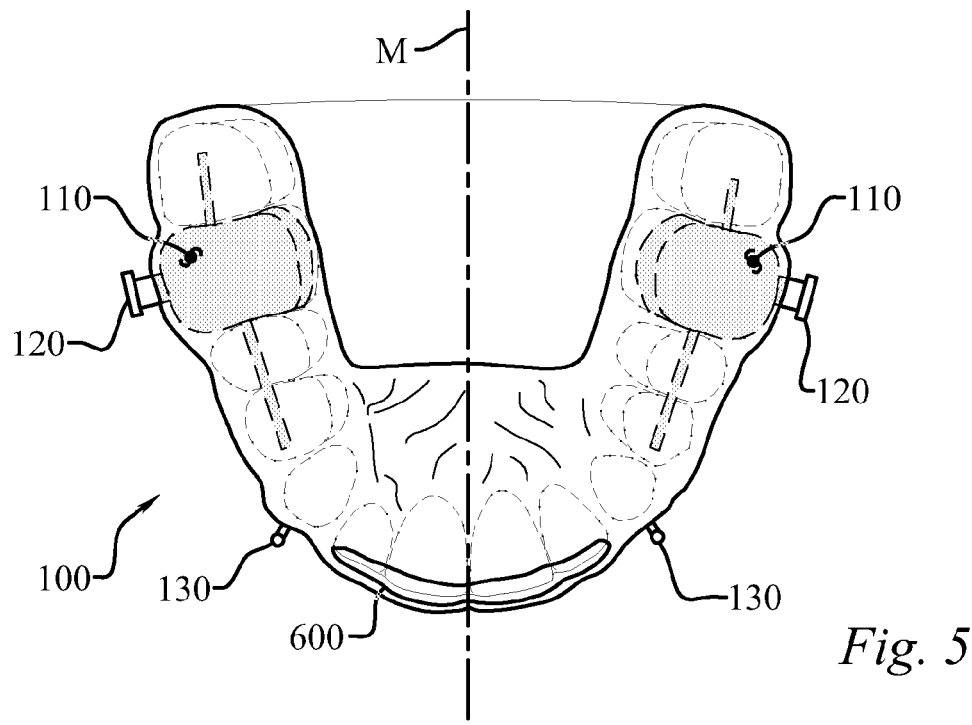
FIG. 5 is an inferior view of a maxillary retainer of a dental orthotic.
Figure 6:
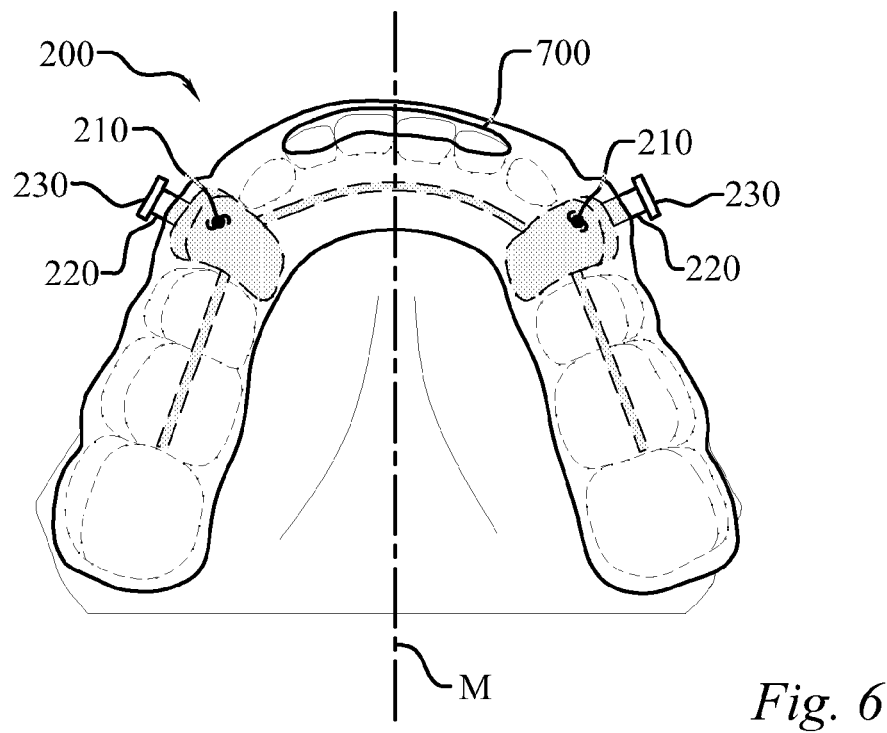
FIG. 6 is a superior view of a mandibular retainer of a dental orthotic.

In one embodiment, seen in FIGS. 5 and 6, the maxilla to strut attachment (120) may include a metal reinforced maxillary reinforcement (110), and the mandible to strut attachment (220) may also include a metal reinforced mandibular reinforcement (210). Similarly, in some embodiments, the maxilla to strut attachment (120) comprises an aramid fiber reinforced maxillary strut attachment (110) and the mandible to strut attachment (220) may comprise an aramid fiber reinforced maxillary reinforcement (210). Embodiments having a combination of metal and aramid reinforcement are particularly envisioned.

Again with reference to FIGS. 3 an 4, in an embodiment, the maxillary retainer (100) may have a maxillary closure attachment (130) and the mandibular retainer (200) may have a mandibular closure attachment (230) with an elastic closure (400) reversibly connecting the maxillary closure attachment (130) and mandibular closure attachment (230). This facilitates a passive closure of the jaw.

The dental orthotic may have jaw displacement indicia (500) on the maxillary retainer (100) and the mandibular retainer (200), seen well in FIG. 4, that cooperate to indicate a relative anterior-posterior relationship between the maxillary retainer (100) and the mandibular retainer (200). This allows the practitioner to see the relative positions of the retainers (100, 200) and allows very small and precise adjustments to be easily seen and measured.

In some embodiments of the dental orthotic (10), seen well in FIGS. 5 and 6, the maxillary retainer (100) may have at least one maxillary fenestration (600), and the mandibular retainer (200) may have at least one mandibular fenestration (700). Embodiments in which both the maxillary retainer (100) and the mandibular retainer (200) have at least one fenestration (600, 700) are particularly envisioned. These fenestrations (600, 700), in at least one effect, provide for greater wearer comfort by allowing more space for tongue movement.

In another embodiment, seen generally in FIGS. 7-12, the dental orthotic (10) comprises at least one resilient strut (800). It can be seen well in FIG. 7 that there may be an anti-obstructive airway dental orthotic (10) with at least one resilient strut (800) having a strut body (870), at least a first at-rest length (820), an anterior end (801), and a posterior end (802). This may in turn cooperate in the maxillary region with a maxillary retainer (100) cooperating with and reversibly attaching to a plurality of maxillary teeth and which has a fixed strut-maxilla attachment (850). Similarly, the dental retainer (10) may have a mandibular retainer (200) cooperating with and reversibly attaching to a plurality of mandibular teeth and having a fixed strut-mandible attachment (860).

Figure 7:
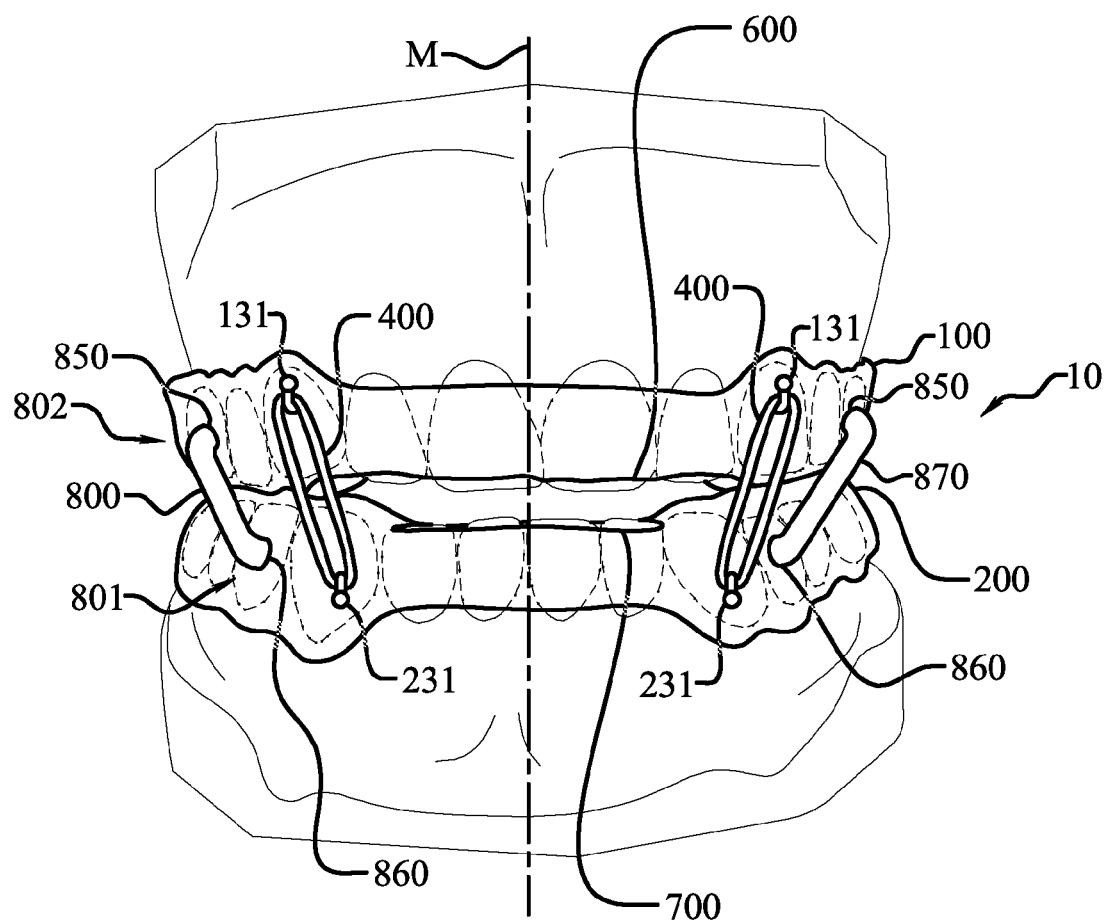
FIG. 7 is a frontal view of another embodiment of a dental orthotic in a wearing position.

The anterior end (801) of the at least one resilient strut (800) may be fixedly attached to the fixed strut-mandible attachment (860) at a fixed strut-mandible attachment point (863) and the posterior end (802) of the at least one resilient strut (800) may be fixedly attached to the fixed strut-maxilla attachment (850) at a fixed strut-maxilla attachment point (853), all seen well in FIGS. 7 and 8.

As described previously, an embodiment, seen well in FIG. 7, may incorporate a maxillary retainer (100) having a maxillary closure attachment (131) and a mandibular retainer (200) having a mandibular closure attachment (231) with an elastic closure (400) reversibly connecting the maxillary closure attachment (131) and mandibular closure attachment (231). Again, this helps facilitate a passive closure of the jaw.

Also as described previously, at least one embodiment may include jaw displacement indicia (500) wherein the resilient strut (800) includes visually perceptible resilient strut length indicia (880), seen well in FIG. 9, that indicate a relative anterior-posterior relationship between the maxillary retainer (100) and the mandibular retainer (200). In the case of the resilient strut (800) embodiments, this is to immediately and accurately identify a predetermined combination of strut (800) length and relative jaw displacement.

In embodiments including a resilient strut (800), the dental orthotic (10) may include a maxillary retainer (100) having at least one maxillary fenestration (600), or a mandibular retainer (200) having at least one mandibular fenestration (700), or some combination of both, as seen well in FIG. 7. As detailed previously, these fenestrations (600, 700) may allow for greater wearer comfort. As would be known by one skilled in the art, the at least one resilient strut (800) may include two resilient struts (800) symmetrically disposed about a midline (M) of the dental orthotic (10), shown by way of example only in FIG. 7.

Embodiments may comprise a system for jaw advancement in which the resilient strut (800) may include at least a resilient strut (800) having a first at-rest length (820) and at least a resilient strut (800) having a second at-rest length (830), seen well in FIG. 9.

Such a system may be invoked, by means of example and not limitation only, by steps that may include: Molding a plurality of maxillary retainers (100), comprising at least a first maxillary retainer (100) and a second maxillary retainer (100), to cooperate with a plurality of maxillary teeth fixed within a maxilla of a human wearer. Similarly, a practitioner may mold a plurality of mandibular retainers (200), comprising at least a first mandibular retainer (200) and a second mandibular retainer (200), to cooperate with a plurality of mandibular teeth fixed within a mandible of the human wearer.

In a later step, the system may comprise attaching a posterior end (802) of at least one resilient strut (800) having a first at-rest length (820), at a fixed strut-maxilla attachment point (853) on the first maxillary retainer (100). Subsequently, a practitioner may attach an anterior end (801) of the at least one resilient strut (800) having a first at-rest length (820), at a fixed strut-mandible attachment point (863) on the first mandibular retainer (200). In such an arrangement, the fixed strut-maxilla attachment (853) is relatively posterior to the fixed strut-mandible attachment point (863) and a first straight line distance (810) between the fixed strut-maxilla attachment point (853) and the fixed strut-mandible attachment point (863) is less than the first at-rest length (820). Thus it can be seen that different resilient strut (800) lengths may produce differing degrees of relative jaw displacement when in use.

Figure 10:
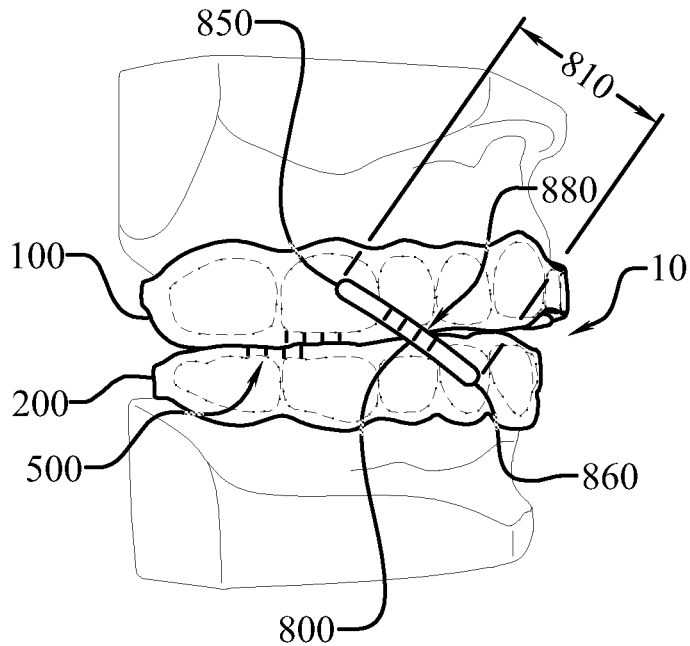
FIG. 10 is a side view of the orthotic of FIG. 7 in a first wearing position.
Figure 11:
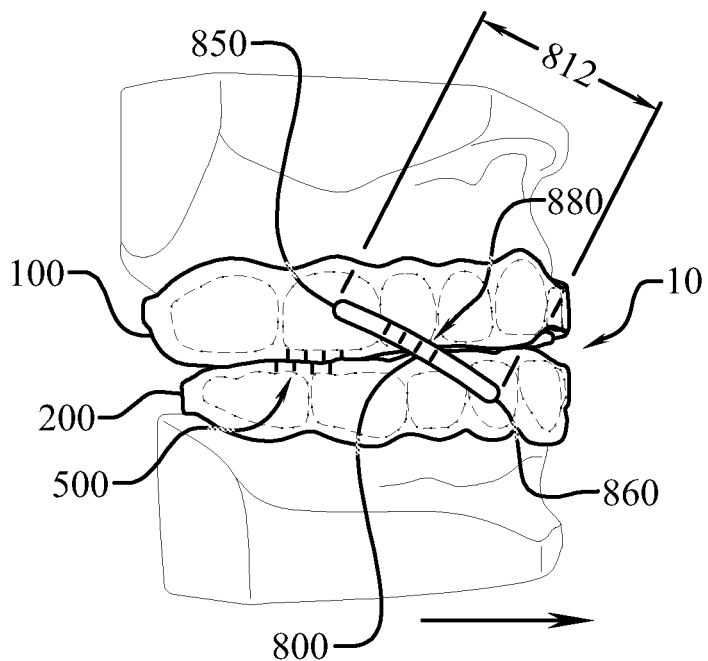
FIG. 11 is the orthotic of FIG. 7 in a second wearing position.
Figure 12:
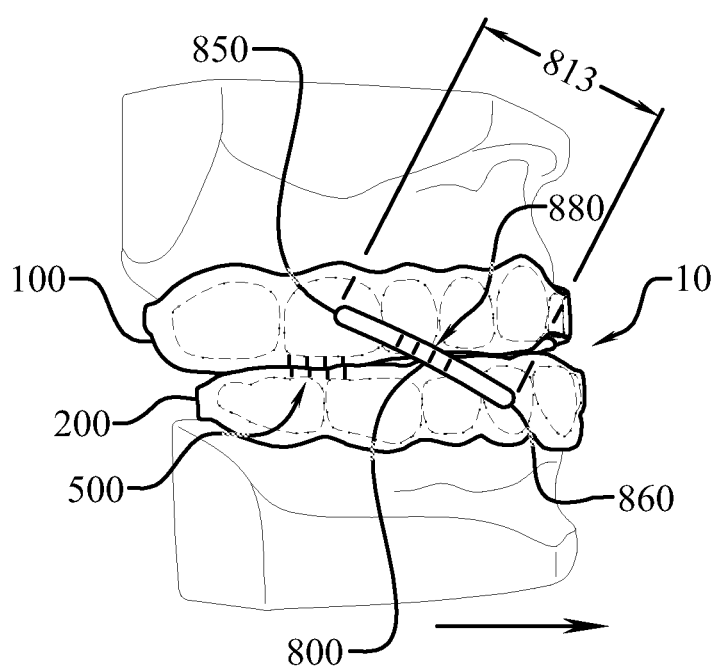
FIG. 12 is the orthotic of FIG. 7 in a third wearing position.

The system may be implemented including at least some of the following steps, as seen by way of example only in FIGS. 10-12: a practitioner may releasably attach the first maxillary retainer (100) to the plurality of maxillary teeth of the human wearer and releasably attach the first mandibular retainer (200) to the plurality of mandibular teeth of the wearer and observe a period of time of attachment of the first maxillary retainer (100) and the first mandibular retainer (200) as joined by the resilient strut (800) separating the retainers (100, 200) by a first straight line distance (810), as seen well in FIG. 10.

One skilled in the art will realize that this effects an advancement in an anterior-posterior direction of the mandible relative to the maxilla of the human wearer and the creation of a resultant second straight line distance (812), seen in FIG. 11, between the fixed strut-maxilla attachment point (853) and the fixed strut-mandible attachment point (863) that is greater than the first straight line distance (810), as may be seen by comparing FIG. 11 with FIG. 10. When the practitioner is satisfied with the degree of advancement, the practitioner may remove the first maxillary retainer (100), the first mandibular retainer (200), and the at least one resilient strut (300) from the human wearer.

Subsequently, the practitioner may attach a posterior end (802) of at least one resilient strut (800) having a second at-rest length (830), at a fixed strut-maxilla attachment point (853) on the second maxillary retainer (100), and attach an anterior end (801) strut (800) to a fixed strut-mandible attachment point (863) on the second mandibular retainer (200). The first straight line distance (810) between the fixed strut-maxilla attachment point (853) and the fixed strut-mandible attachment point (863) is less than the second at-rest length (830), thereby allowing the resilient strut (800) to exert an elastic pressure favoring jaw advancement.

As described earlier, the practitioner may then releasably attach the second maxillary retainer (100) to the plurality of maxillary teeth of the human wearer and releasably attach the second mandibular retainer (200) to the plurality of mandibular teeth of the wearer. By observing a period of time of attachment of the maxillary retainer (100) and the mandibular retainer (200); an advancement in an anterior-posterior direction of the mandible relative to the maxilla of the human wearer is effected. This results in the creation of a resultant third straight line distance (813), as seen well in FIG. 12, between the fixed strut-maxilla attachment point (853) and the fixed strut-mandible attachment point (863) that is greater than the second straight line distance (812).

Again, the practitioner may observe a period of time of attachment of the second maxillary retainer (100) and the second mandibular retainer (200); and by repeating at least the steps above, gradually over time produce a final desired advancement in an anterior-posterior direction of the mandible relative to the maxilla of the human wearer. The progression may be seen in illustrative example only by the gradual progression in jaw displacement seen in the series: FIG. 10; FIG. 11; FIG. 12.

One skilled in the art will know that the assessment of a final desired jaw advancement may be made with a number of methods, which may include but are not limited to; subjective sense of airway improvement by the wearer, a measurement of a resting heart rate at an ambient atmosphere of the wearer, the achievement of an advancement to a predetermined amount of advancement by objective metrics, measuring and comparing resting arterial blood oxygen saturation level at an ambient atmosphere of the wearer to predetermined levels, and/or measuring and comparing a resting heart rate at an ambient atmosphere of the wearer to predetermined levels.

Numerous alterations, modifications, and variations of the preferred embodiments disclosed herein will be apparent to those skilled in the art and they are all anticipated and contemplated to be within the spirit and scope of the disclosed dental orthotic (10). For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the dental orthotic (10) are described herein, it is to be understood that the practice of such additional modifications and variations and the equivalents thereof, are within the spirit and scope of the dental orthotic (10) as disclosed herein. The corresponding structures, materials, acts, and equivalents of all means or step plus function elements in the claims below are intended to include any structure, material, or acts for performing the functions in combination with other claimed elements as specifically claimed.

I claim:

1. A method for advancing an anterior-posterior of a mandible relative to a maxilla comprising the steps of:
   a) molding a plurality of maxillary retainers (100), comprising at least a first maxillary retainer (100) and a second maxillary retainer (100), to cooperate with a plurality of maxillary teeth fixed within a maxilla of a human wearer;
   b) molding a plurality of mandibular retainers (200), comprising at least a first mandibular retainer (200) and a second mandibular retainer (200), to cooperate with a plurality of mandibular teeth fixed within a mandible of the human wearer;
   c) attaching a posterior end (802) of at least one resilient strut (800) having a first at-rest length (820), at a fixed strut-maxilla attachment point (853) on the first maxillary retainer (100), and attaching an anterior end (801) of the at least one resilient strut (800) having a first at-rest length (820), at a fixed strut-mandible attachment point (863) on the first mandibular retainer (200), wherein the fixed strut-maxilla attachment (853) is relatively posterior to the fixed strut-mandible attachment point (863) and a first straight line distance (810) between the fixed strut-maxilla attachment point (853) and the fixed strut-mandible attachment point (863) is less than the first at-rest length (820);
   d) releasably attaching the first maxillary retainer (100) to the plurality of maxillary teeth of the human wearer and releasably attaching the first mandibular retainer (200) to the plurality of mandibular teeth of the wearer and observing a period of time of attachment of the first maxillary retainer (100) and the first mandibular retainer (200); thereby effecting an advancement in an anterior-posterior direction of the mandible relative to the maxilla of the human wearer and the creation of a resultant second straight line distance (812) between the fixed strut-maxilla attachment point (853) and the fixed strut-mandible attachment point (863) that is greater than the first straight line distance (810);
   e) removing the first maxillary retainer (100), the first mandibular retainer (200), and the at least one resilient strut (*00) from the human wearer;
   f) attaching a posterior end (802) of at least one resilient strut (800) having a second at-rest length (830), at a fixed strut-maxilla attachment point (853) on the second maxillary retainer (100), and attaching an anterior end (801) of the at least one resilient strut (800) having a second at-rest length (830), at a fixed strut-mandible attachment point (863) on the second mandibular retainer (200) and the first straight line distance (810) between the fixed strut-maxilla attachment point (853) and the fixed strut-mandible attachment point (863) is less than the second at-rest length (830);
   g) releasably attaching the second maxillary retainer (100) to the plurality of maxillary teeth of the human wearer and releasably attaching the second mandibular retainer (200) to the plurality of mandibular teeth of the wearer and observing a period of time of attachment of the second maxillary retainer (100) and the second mandibular retainer (200); thereby effecting an advancement in an anterior-posterior direction of the mandible relative to the maxilla of the human wearer and the creation of a resultant third straight line distance (813) between the fixed strut-maxilla attachment point (853) and the fixed strut-mandible attachment point (863) that is greater than the second straight line distance (812); and
   h) repeating the steps a)-h) above as necessary to achieve a final desired advancement in an anterior-posterior direction of the mandible relative to the maxilla of the human wearer.

2. The method according to claim 1, wherein the step of observing a period of time of attachment includes a measurement of a resting heart rate at an ambient atmosphere of the wearer.

3. The method according to claim 1, wherein the step of repeating steps a)-h) as necessary to achieve a final desired advancement in an anterior-posterior direction of the mandible relative to the maxilla of the human wearer includes a step of achieving an advancement to a predetermined amount of advancement.

4. The method according to claim 1, wherein the step of repeating steps a)-h) as necessary to achieve a final desired advancement in an anterior-posterior direction of the mandible relative to the maxilla of the human wearer includes a step of measuring and comparing resting arterial blood oxygen saturation level at an ambient atmosphere of the wearer to predetermined levels.

5. The method according to claim 1, wherein the step of repeating steps a)-h) as necessary to achieve a final desired advancement in an anterior-posterior direction of the mandible relative to the maxilla of the human includes a step of measuring and comparing a resting heart rate at an ambient atmosphere of the wearer to predetermined levels.

\* \* \* \* \*